(12) United States Patent
Schmidt et al.

(10) Patent No.: US 8,353,195 B2
(45) Date of Patent: Jan. 15, 2013

(54) MINIATURIZED GAS CHROMATOGRAPHY MODULE WITH PRE-STAGE MINIATURIZED UNIT

(75) Inventors: Tobias Schmidt, Steinhorst (DE); Volker Klose, Wentorf (DE)

(73) Assignee: SLS Micro Technology GmbH, Hamburg (DE)

( * ) Notice: Subject to any disclaimer, the term of this patent is extended or adjusted under 35 U.S.C. 154(b) by 340 days.

(21) Appl. No.: 12/601,961

(22) PCT Filed: Aug. 22, 2007

(86) PCT No.: PCT/EP2007/007386
§ 371 (c)(1),
(2), (4) Date: Jan. 25, 2010

(87) PCT Pub. No.: WO2009/024171
PCT Pub. Date: Feb. 26, 2009

(65) Prior Publication Data
US 2010/0186481 A1 Jul. 29, 2010

(51) Int. Cl.
*G01N 30/04* (2006.01)
*G01N 30/66* (2006.01)

(52) U.S. Cl. .................................. 73/23.42; 73/23.41

(58) Field of Classification Search .............. 73/23.41, 73/23.42, 28.06
See application file for complete search history.

(56) References Cited

U.S. PATENT DOCUMENTS

| | | |
|---|---|---|
| 3,162,035 A | 12/1964 | Kent |
| 4,935,040 A | 6/1990 | Goedert |
| 5,066,533 A | 11/1991 | America et al. |
| 5,522,988 A | 6/1996 | Cortes et al. |
| 2006/0196247 A1 | 9/2006 | Gamache et al. |

FOREIGN PATENT DOCUMENTS

| | | |
|---|---|---|
| CN | 1 707 261 | 12/2005 |
| DE | 203 00 701 | 3/2003 |
| DE | 20 2005 011 825 | 11/2006 |
| EP | 0 989 401 | 3/2000 |
| JP | 2000 146886 | 5/2000 |
| WO | WO 2004/065955 | 8/2004 |
| WO | WO 2006/042727 | 4/2006 |

OTHER PUBLICATIONS

Sorge et al., "Fully integrated thermal conductivity sensor for gas chromatography without dead volume," *Sensors and Actuators A*, Dec. 1997, vol. 63, No. 3, pp. 191-195.

*Primary Examiner* — Lisa Caputo
*Assistant Examiner* — Punam Roy
(74) *Attorney, Agent, or Firm* — Saliwanchik, Lloyd & Eisenchenk

(57) ABSTRACT

The invention relates to a miniaturized gas chromatography module, comprising: a gas injector unit having a gas injector sample inlet and outlet, the gas injector inlet being connectable with a source of a substance to be analyzed, a separation column having a separation column inlet and outlet, the separation column inlet being in fluid communication with the gas injector sample outlet, a thermal conductivity sensor having a sensor inlet and outlet, the sensor inlet being in fluid communication with the separation column outlet. The invention addresses the problem to broaden the field of application of such gas chromatography module. This is achieved by providing a pre-stage injector having a pre-stage injector sample inlet and outlet, the pre-stage injector sample inlet being connectable with the source of the substance to be analyzed, a pre-stage module having a module inlet and outlet, the module inlet being in fluid communication with the pre-stage injector sample. outlet and the module outlet being in fluid communication with the gas injector inlet, wherein the pre-stage module is adapted to transfer heat to a substance flowing from the module inlet to the module outlet.

23 Claims, 7 Drawing Sheets

MINIATURIZED GAS CHROMATOGRAPHY MODULE WITH PRE-STAGE MINIATURIZED UNIT

CROSS-REFERENCE TO A RELATED APPLICATION

This application is a National Stage Application of International Application No. PCT/EP2007/007386, filed Aug. 22, 2007, which is incorporated herein by reference in its entirety.

The invention relates to a miniaturized gas chromatography module, comprising: a gas injector unit having a gas injector sample inlet and outlet, the gas injector inlet being connectable with a source of a substance to be analyzed, a separation column having a separation column inlet and outlet, the separation column inlet being in fluid communication with the gas injector sample outlet, a thermal conductivity sensor having a sensor inlet and outlet, the sensor inlet being in fluid communication with the separation column outlet. The invention further relates to a method of analyzing a substance using a miniaturized gas chromatography module.

Devices and methods for gas chromatographical analysis are well-known. Such devices generally include large-scale separation columns and require significant amounts of the samples which are to be analyzed. Whereas the precision, resolution and the range of substances which can be analyzed of such conventional gas chromatographical devices and methods is excellent for a number of applications, the size of the device, the energy consumption and the time of the analysis is not satisfying the requirements of several applications wherein an analysis is desired in a quick and cost-efficient manner.

From EP 1 588 156 B1 a miniaturized gas chromatograph is known allowing such quick and cost-efficient analysis of a variety of substances. The gas chromatograph consists of a miniaturized sample injector, a miniaturized separation column and a miniaturized thermal conductivity sensor.

Whereas a large number of samples can be analyzed with such miniaturized gas chromatograph, the need exists to provide miniaturized gas chromatographs having a higher precision and resolution than the prior art miniaturized gas chromatographs.

A further problem associated with prior art miniaturized gas chromatographs is due to the fact that only gaseous samples can be analyzed thus reducing the number of substances which can be analyzed significantly. Thus, the need exists to provide a miniaturized gas chromatograph allowing to analyze additional substances, in particular liquid substances.

According to the invention, a solution to the above-referenced problems is provided by providing a miniaturized gas chromatography module as referenced above which is characterized by
- a pre-stage injector having a pre-stage injector inlet and outlet, the pre-stage injector inlet being connectable with a source of the substance to be analyzed,
- a pre-stage microtechnological module having a module inlet and outlet, the module inlet being in fluid communication with the pre-stage injector sample outlet and the module outlet being in fluid communication with the gas injector inlet,
- wherein the pre-stage microtechnological module is adapted to transfer heat to a substance flowing from the module inlet to the module outlet.

The gas chromatography module according to the invention comprises a pre-stage injector and a pre-stage miniaturized module. The pre-stage injector is adapted to separate or extract a small, pre-determined amount from a continuous or quasi-continuous flow of a substance which is to be analyzed. Thus, a sample of this substance is provided which can be delivered to the other components of the module for analysis. The pre-stage injector may be specifically adapted to extract a sample from a gaseous or liquid substance or may be adapted to handle both liquid and gaseous substances. It is to be understood that in certain applications the pre-stage injector could be omitted.

The sample extracted by the pre-stage injector is delivered to the pre-stage miniaturized module. This pre-stage miniaturized module may comprise a cavity like a small chamber, a channel, a plurality of chambers connected via channels or the like which are preferably provided in a wafer construction like two wafers bonded to each other after manufacturing the geometry of the chambers and channels in the surface of each wafer. The pre-stage miniaturized module is adapted to transfer heat to the sample flowing through the chambers, channels or the like. This can easily be achieved by connecting a heat element to the module or by heating the module itself, e.g. by electrical resistance heating.

A first important advantage of the miniaturized gas chromatography module according to the invention is that the sample to be analyzed is pre-heated in the pre-stage miniaturized module which may enhance precision and resolution of the subsequent injection process and separation process in the gas injector and separation column. The additional pre-stage heating may homogenize the sample thus allowing a precise dosage of the sample in the subsequent injection process in the gas injector. Any liquid partitions like droplets will be vaporized by the heating process and thus not adversely affect the subsequent analyzing steps.

Still further, the miniaturized gas chromatography module according to the invention allows for a number of improved analyzing procedures by pre-stage treatment of the substance to be analyzed in the pre-stage injector and pre-stage miniaturized module.

According to a first preferred embodiment, the pre-stage injector is adapted to provide a predetermined amount of a liquid substance to the pre-stage module and the pre-stage module is adapted to vaporize said amount of the liquid fluid and provide the vaporized liquid to the gas injector.

According to this embodiment, the miniaturized gas chromatography module is able to analyze liquid substances without using large-scaled devices for handling, pre-processing and storing the substance which is to be analyzed. The pre-stage injector is adapted to inject a pre-determined sample amount extracted from the liquid substance. Usually, the substance which is to be analyzed is to be taken by the miniaturized gas chromatography module from a continuous flow. It is desirable to only take a small amount from this continuous flow. Further, it is desirable that the analyzing process can be repeated after a short time, i.e. to provide a high sampling rate. This requires a high frequency of the taking of the samples which are to be analyzed.

According to the first preferred embodiment, the samples are taken from a continuous flow of a liquid substance. The pre-stage injector thus requires specific dimensions of its channels and functional elements like a switching element moveable within an injector housing or the like. Using such specifically adapted injector, a small, pre-determined amount of the liquid substance is extracted from the continuous flow and delivered to the pre-stage miniaturized module.

The pre-stage miniaturized module is adapted to transfer an amount of heat to this liquid sample which is sufficient to completely vaporize the liquid sample. For this purpose, the pre-stage miniaturized module may comprise a heated chamber, into which the liquid sample is delivered and wherein the liquid sample is completely vaporized or the pre-stage miniaturized module may comprise a heated channel through which the liquid sample is flowing and along which the liquid sample is completely vaporized.

It is to be understood that the vaporization of the liquid sample results in a significant expansion process, thus producing a large volume of the substance which is to be analyzed. Usually, such large volume cannot be used to be introduced directly into a separation column because it lacks a well-defined beginning and end and will extend along a too long length section of the separation column, thus reducing the precision and resolution of the analysis. However, it should be understood that by further improvement of the pre-stage injector allowing to extract a very small liquid amount from the continuous flow of the liquid substance and by defining a well-defined beginning and end of the vaporized volume in the pre-stage miniaturized module it may be possible to even directly insert the vaporized sample volume extracted by the pre-stage injector into a separation column for analyzing the substance.

However, it is preferred to deliver the vaporized substance to the gas injector unit in order to extract a well-defined small volume from this vaporized sample volume which will allow a precise analysis of the substance in the subsequent separation step and detection step. The gas injector unit may be designed as described in EP 1 588 156 B1 as mentioned in the introductory portion of this description or may be of any further improved design. It is to be understood that the gas injector unit must be controlled in such a way to extract the sample to be taken from the vaporized sample at a specific time since this sample is not taken from a continuous flow of a substance but from a limited volume as provided by the pre-stage injector.

Subsequently, the sample extracted by the gas injector unit is delivered to the separation column and separated into several fractions therein which are subsequently detected by the thermal conductivity sensor to identify the type of molecules contained in the substance to be analyzed. Thus, according to the invention, a miniaturized gas chromatography module is provided which is capable of analyzing liquid substances in a fast and cost-efficient manner.

According to a second preferred embodiment the pre-stage injector is adapted to provide a predetermined amount of a gaseous substance to the pre-stage module, wherein the pre-stage module is a pre-stage separation column adapted to separate the flow of gas into a plurality of fractions and to sequentially provide said fractions to said gas injector.

With this preferred embodiment it is possible to analyze a substance using a multi-stage analysis two sequential analyzing steps in the separation columns provided by the module according to the invention. Such embodiment is of particular advantage when analyzing substances which include molecules that have very high molecular weights and molecules that have significantly lower molecular weights. Usually, separation columns which are adapted to separate molecules of very high molecular weight from molecules with significantly lower molecular weight are not capable of separating molecules which molecular weight is close to each other. The preferred embodiment allows a detailed analysis of substances which include molecules within a broad range of molecular weights. In the pre-stage separation column the substance is separated into a number of fractions thus separating the very high molecular weight molecules from those having significantly lower molecular weight. Hereafter, said fractions are provided to the gas injector unit in a sequential order. Fractions which shall not be examined further can be directed to a waste exit by the gas injector unit. Fractions which shall be analyzed further can be extracted from the sequential order of fractions by the gas injector unit and provided to the separation column which now takes the position of a second separation column after the first (pre-stage) separation column. The second separation column should preferably be adapted to separate one or more of the fractions which had been provided by the pre-stage separation column into more detailed fractions. Usually, such separation columns capable of separating fractions in such detailed fractions are designed to handle molecules of a rather narrow range of molecular weights. Thus, a fraction including molecules of such narrow range of molecular weights must be selected to be provided to the separation column to the gas injector unit. In the separation column this specific fraction or these specific fractions are then subdivided further allowing a detailed analysis of the fraction.

When providing such cascade of a pre-stage separation column and a subsequent separation column it is further preferred that the gas injector is a four port valve having a first valve inlet in fluid communication with the outlet of the pre-stage separation column, a second valve inlet in fluid communication with a source of a carrier gas, a first valve outlet in fluid communication with the separation column inlet, a second valve outlet in fluid communication with a waste exit and a valve body coupling in a first position the first valve inlet to the second valve outlet and in a second position the first valve inlet to the second valve outlet. Using such four port valve will allow to direct those fractions of the substance to be analyzed to a waste exit which shall not be investigated further and to direct the fraction or the fractions which shall be analyzed further to the separation column for further separation. Preferably, the four port valve is a miniaturized valve unit to reduce size and energy consumption of the whole module.

Still further, when providing the cascade of separation columns as previously described, it is preferred to further include a pre-stage thermal conductivity sensor coupled between the pre-stage separation column outlet and the first valve inlet to analyze fractions of the substance as provided by the pre-stage separation column, a control device adapted to receive a signal from the pre-stage thermal conductivity sensor and to switch the four port valve between the first and second position to provide a selected fraction of the gas to the separation column inlet. Such pre-stage thermal conductivity sensor will allow to identify the molecular weight or molecular weight ranges of the fractions which had been separated by the pre-stage separation column. This will allow to selectively direct these fractions to the separation column or an exit, e.g. by using the four port valve as described beforehand or a gas injector unit. For this purpose, a control device is connected to the pre-stage thermal conductivity sensor to receive signals indicating the molecular weight (range) of a fraction which passes the thermal conductivity sensor and the time at which the fraction passes the sensor. From this, the time at which the fraction will enter into the gas injector can be calculated and it can be decided whether this fraction shall be investigated further in the subsequent separation column or shall be directed to an exit. The control device may be adapted to receive input from a user of the module to select those molecular weight ranges which shall be investigated further in the subsequent separation column.

Still further, it is preferred that the module according to the invention comprises at least one supplemental analyzing unit, the analyzing unit comprising:

a supplemental valve unit having a supplemental valve inlet and outlet, a supplemental separation column having a supplemental column inlet and outlet, the supplemental column inlet being in fluid communication with the supplemental valve outlet, a supplemental thermal conductivity sensor having a supplemental sensor inlet and outlet, the supplemental sensor inlet being in fluid communication with the supplemental column outlet.

Such supplemental analyzing unit may be combined with the pre-stage injector and pre-stage module being adapted to provide a predetermined amount of a liquid substance and to vaporize said amount or with the pre-stage injector and pre-stage module being adapted to provide a predetermined amount of a gaseous substance and to separate that gaseous substance into a plurality of fractions. The supplemental analyzing unit is provided to further improve precision and cost efficiency of the analysis which can be performed with the module according to the invention. Preferably, the supplemental analyzing unit is coupled to the outlet of the separation column, in particular to the outlet of said thermal conductivity sensor. By this, a sequential arrangement of the separation column and its associated thermal conductivity sensor and the supplemental analyzing unit is provided to allow a cascaded arrangement of analyzing units. In case that the pre-stage module is adapted to vaporize a liquid substance to be analyzed, such supplemental analyzing unit will allow the precise and cost efficient multistage analysis of substances including a broad range of molecular weights as described beforehand. In case that the pre-stage module is a separation column, the supplemental analyzing unit will allow to further analyze a fraction which is separated by the separation column from the fractions separated by the pre-stage separation column. Thus, a cascade of in total three separation columns is provided to allow a three step separating process and a detailed analysis of molecules being within a very narrow range of molecular weights.

Still further, it is preferred that the module according to the invention comprises a plurality of supplemental analyzing units, wherein the plurality of units are connected in series to each other by providing a fluid communication between the supplemental sensor outlet of a preceding, supplemental analysing unit to the supplemental valve inlet of a following supplemental analysing unit. Such arrangement will allow to provide a cascaded arrangement of separation columns, each being adapted to separate within a specific range of molecular weights and thus allowing to analyze a substance in a very precise manner, in particular to analyze a specific narrow range of molecular weights in detail.

According to a still further preferred embodiment the module according to the invention comprises a distribution valve unit and valve unit having a distribution valve inlet and a plurality of distribution valve outlets and a plurality of parallel supplemental analysing units, each analysing unit comprising:

a supplemental separation column having a supplemental column inlet and outlet, the supplemental column inlet being in fluid communication with an outlet of the distribution supplemental valve, a supplemental thermal conductivity sensor having a supplemental sensor inlet and outlet, the supplemental sensor inlet being in fluid communication with the supplemental column outlet.

a control device adapted to receive a signal from the pre-stage thermal conductivity sensor and to switch the distribution valve between a plurality of positions to sequentially provide selected fractions of the gas to each distribution valve outlet.

According to this embodiment, at least two separation columns are provided which are arranged in parallel to each other, thus allowing a parallel separation of the substance to be analyzed or a fraction of this substance. In particular, with this embodiment it is possible to separate a substance in a pre-stage separation column and to subsequently provide a first fraction or a first plurality of fractions to a first one of two parallel separation columns and to provide another, second fraction or plurality of fractions to a second one of the two parallel separation columns. The first separation column may be adapted to separate a specific range of molecular weights whereas the second separation column may be adapted to separate another, different specific range of molecular weights from each other, thus allowing to analyze a substance in such a way to do a pre-stage separation and to subsequently analyze two or more molecular weight ranges in detail and in a parallel process. It is to be understood that even more than two parallel separation columns can be provided.

Using such parallel arrangement of separation columns it is further preferred that at least one of the supplemental thermal conductivity sensors of the parallel supplemental analysing units is followed by at least one supplemental analyzing unit coupled in series according to the preceding claim 7. According to this preferred embodiment, a number of parallel analyzing units is provided, each analyzing unit comprising at least one separation column and at least one of the analyzing units comprising two separation columns which are arranged in a sequential order to provide a cascaded multi-stage analysis as described beforehand.

According to further preferred embodiments the gas injector unit or the pre-stage gas injector comprises:

an injector carrier gas inlet connectable to a source of a carrier gas, an injector waste outlet connectable to a waste exit or connectable to the source of the substance to be analysed, wherein the inlets and outlets are provided in an injector housing the housing further comprising a moveable injector body which can be moved from a first injector body position wherein the substance to be analysed is flowing from the injector sample inlet through a sample storage section to the pre-stage waste outlet and a second injector body position wherein the carrier gas is flowing from the injector carrier gas inlet through the sample storage section to the injector sample outlet thus providing a predetermined amount of the substance to be analysed to the injector sample outlet.

According to these embodiments, a miniaturized pre-stage injector or gas injector unit is provided allowing a cost-efficient and precise injection of a liquid or gaseous amount of a substance to be analyzed.

According to another aspect of the invention, a method for analyzing a substance is provided, the method comprising the steps of providing a flow of the substance to a gas injector sample inlet of a gas injector unit, extracting a predetermined amount from the flow of the substance by the gas injector unit and providing said amount from a gas injector sample outlet to a separation column inlet of a separation column, separating said amount into a plurality of fractions of the substance by the separation column and providing said fractions to a sensor inlet of a thermal conductivity sensor, determining the time intervals between the time at which the extracted amount of the substance was provided from the gas injector to the separation column and the time at which each fraction passes the thermal conductivity sensor, comparing the time intervals with pre-known time intervals stored in a list associated with pre-known substances and thus identifying the substance contained in each fraction, wherein the following steps are done before providing the substance to the gas injector unit:

providing a continuous flow of the substance to a pre-stage injector inlet of a pre-stage injector, extracting a predetermined amount from the continuous flow by the pre-stage injector and providing said amount to a module inlet of a pre-stage module, transferring heat from a surface of the pre-stage module to said amount of said substance, and providing said amount of said substance from an outlet of said pre-stage module to said gas injector inlet.

According to this method of the invention it is possible to significantly improve the precision and cost efficiency of prior art analyzing methods. The method is based on using miniaturized analyzing components. By providing steps which extract a predetermined amount by a pre-stage injector and transferring heat to said amount the precision of the analysis can be enhanced significantly, as described beforehand. The such pre-treated amount of the substance to be analyzed is then provided to the inlet of the gas injector unit and analysis of this pre-determined amount is conducted as described above in the separation column and the thermal conductivity sensor.

It is particularly preferred that the substance provided to the pre-stage injector is a liquid substance, said amount of said liquid substance is vaporized in said pre-stage module and the vaporized liquid is provided to the gas injector. By vaporizing the liquid substance it is possible to analyze liquid substances in miniaturized gas chromatographic analyzing modules, thus significantly lowering the costs for analysis of such substances and significantly increasing the precision of analysis.

Still further, it is alternatively preferred that said substance provided to said pre-stage injector is gaseous, wherein said amount of said gaseous substance is separated into a plurality of fractions in said pre-stage module being a pre-stage separation column, said fractions are sequentially provided to a pre-stage thermal conductivity sensor to analyze fractions of the substance as provided by the pre-stage separation column, said fractions are provided from the pre-stage thermal conductivity sensor to the gas injector and at least one selected fraction, preferably a selected plurality of said fractions, but not all fractions, are provided to the separation column inlet, wherein a control device receives a signal from the pre-stage thermal conductivity sensor and switches the gas injector to provide said selected fractions of the gas to the separation column inlet. Using this preferred embodiment of the method according to the invention a sequential analysis of a substance in at least two separation columns each followed by a thermal conductivity sensor is provided, thus allowing a detailed analysis of at least one fraction including molecules within a specific range of molecular weights. Using such method, a first separation column can be used which is capable of separating molecules lying in a broad range of molecular weights and a second separation column can be subsequently used which is capable of separating molecules lying in a rather narrow range of molecular weights. The second separation column is used to separate a selected fraction which was previously separated by the first separation column and to provide details of this selected fraction.

According to a still further embodiment it is preferred that at least selected fraction, preferably a selected plurality of said fractions, but not all fractions, are further analysed in at least one supplemental analysing unit by:

providing all fractions from the outlet of the thermal conductivity sensor to an inlet of a supplemental valve unit, extracting said selected fraction(s) by said supplemental valve unit and providing said selected fraction(s) to a supplemental separation column, separating said fractions(s) into a plurality of sub-fractions of the substance by the supplemental separation column and providing said sub-fractions to a sensor inlet of a supplemental thermal conductivity sensor, determining the time intervals between the time at which said selected fraction(s) of the substance was/were provided to the supplemental separation column and the time at which each sub-fraction passes the supplemental thermal conductivity sensor, comparing the time intervals with pre-known time intervals stored in a list associated with pre-known substances and thus identifying the substance contained in each sub-fraction.

According to this preferred embodiment, a sequential multi-stage analysis in a plurality of steps is provided thus allowing to provide detailed information of a specific molecular weight range contained in the substance to be analyzed.

The supplemental analysis can alternatively be conducted parallel to each other by providing selected fractions to a first separation column and another selected fraction to a second separation column. Reference is made to the parallel arrangement of separation columns as described beforehand. Additionally, in the parallel analysis the analysis can be performed in a cascade of a serial arrangement thus allowing to sequentially subdivide the substance into fractions, sub-fractions, sub-sub-fractions and so on and to provide detailed analysis of such divided sub-fraction or sub-sub-fraction.

Preferred embodiments of the invention are described referring to the figures. In the figures, FIG. 1 shows a schematical order of processes or the components associated to such respective processes for analysis of a liquid substance in a one stage separating process.

Figure 2:
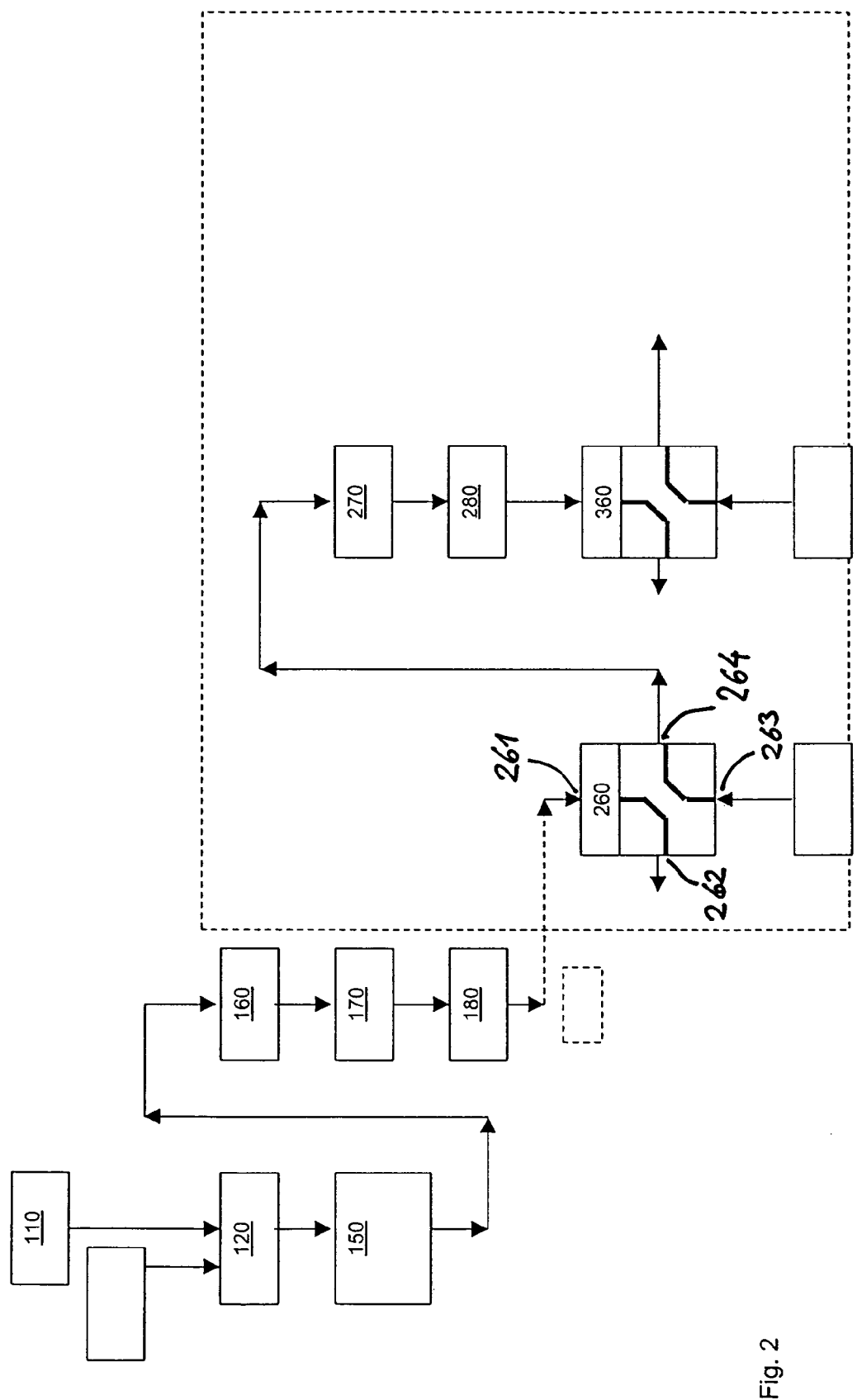
Figure 3:
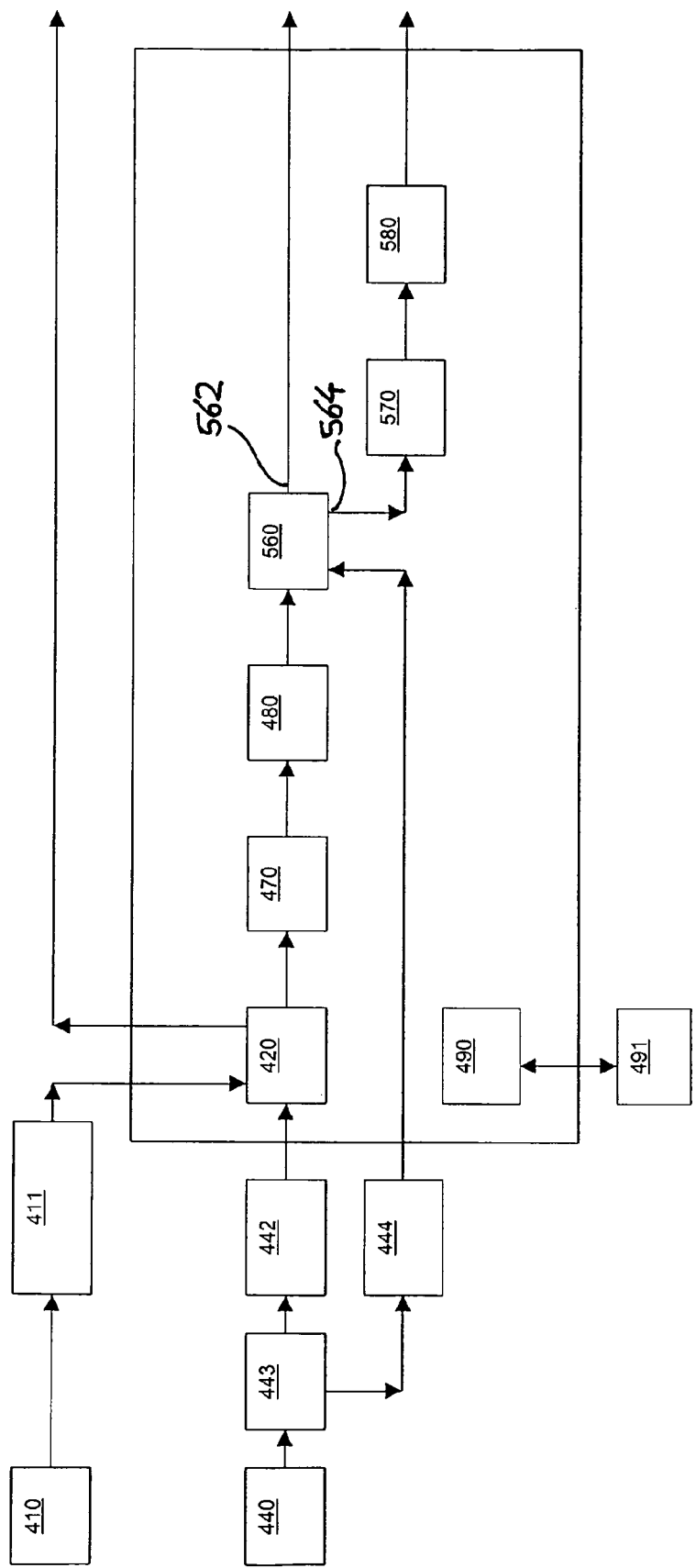
Figure 4:
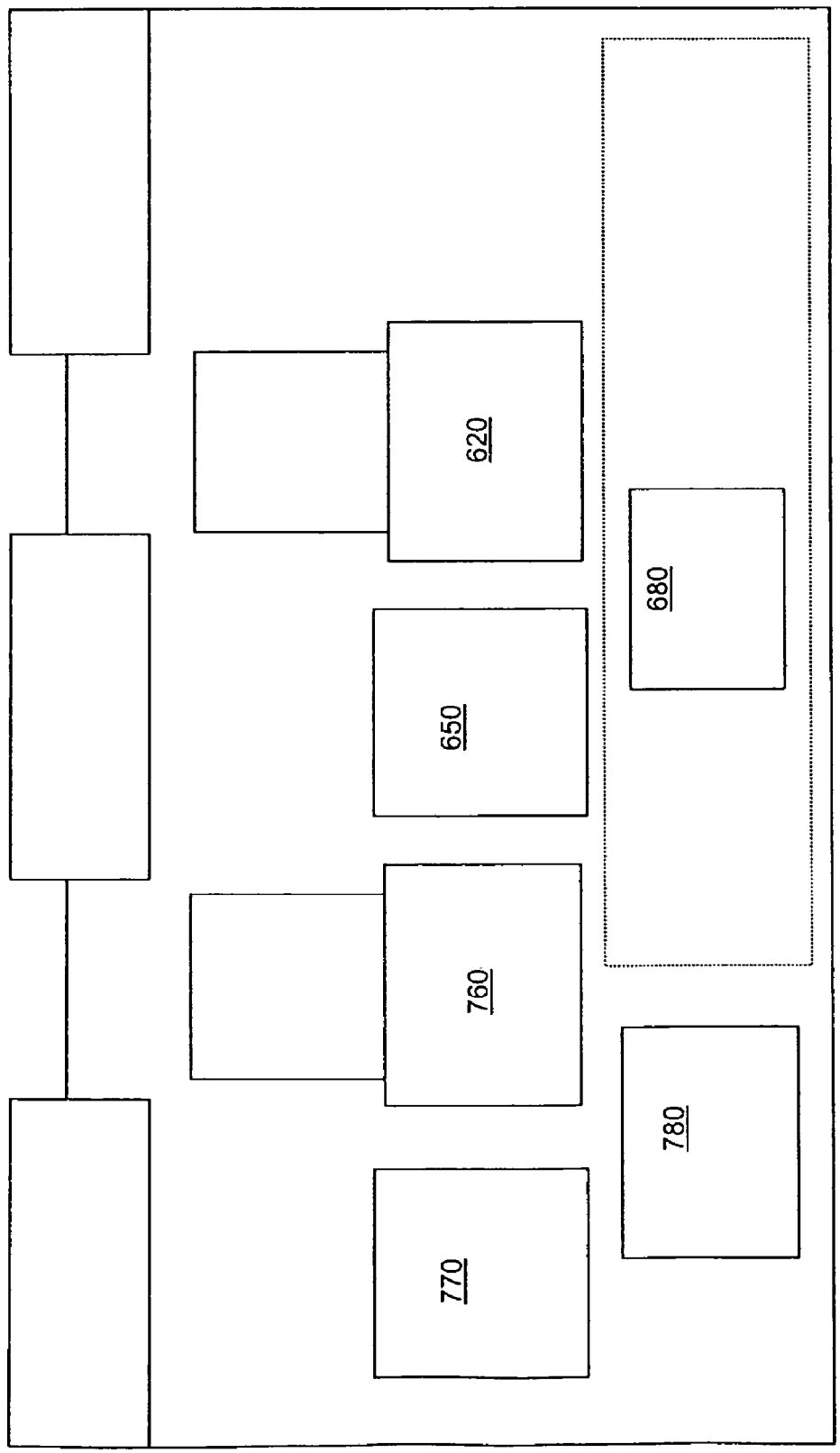
Figure 5:
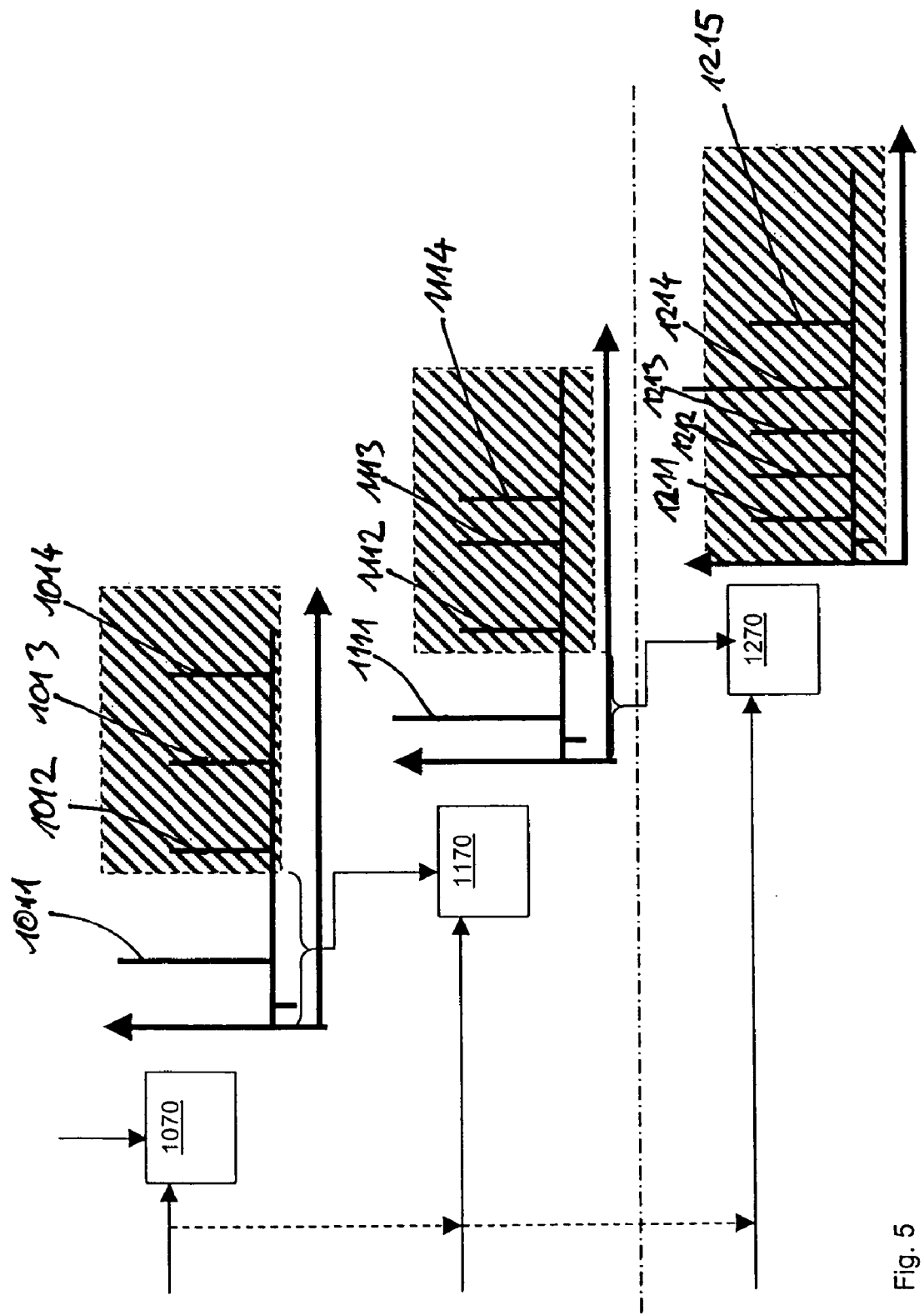

FIG. 2 shows a schematical order of processes or the components associated to the respective processes for the analysis of a liquid substance in a two stage separating process, FIG. 3 shows a schematical order of processes or the components associated to such respective processes for analyzing a gaseous substance in a two stage separating process, FIG. 4 shows a schematical arrangement of the components for analyzing a liquid substance in a one stage separation process or for analyzing a gaseous substance in a two stage analyzing process on one printed circuit board, and FIG. 5 shows a schematical diagram of a multi-stage analysis in a serial cascade of separation columns.

Figure 1:
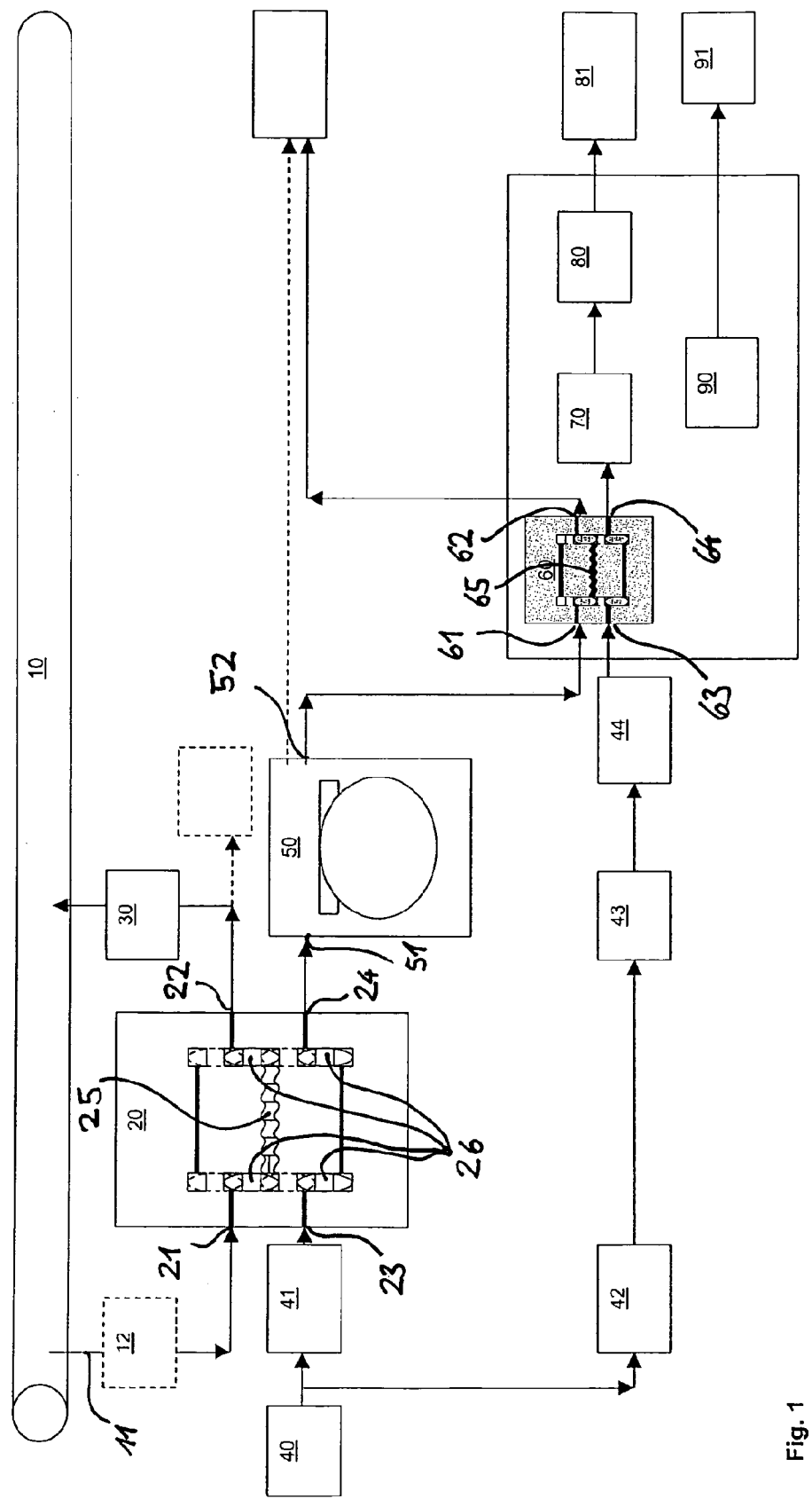
FIG. 1a shows a partial view of FIG. 1 in detail according to a first embodiment.
FIG. 1b shows a partial view of FIG. 1 in detail according to a second embodiment.

Referring first to FIG. 1, a substance to be analyzed is flowing through a pipe 10 which may be a pipe involved in a process or a standard bypass coupled to such pipe.

Using a coupling 11, an inlet 21 of a micro fluid injector is coupled to the pipe 10, optionally including a sample pump 12 to pump the sample from the coupling 11 to the inlet 21, as depicted in dotted lines in FIG. 1.

The micro fluid injector comprises an outlet 22 through which the sample can be redirected to be reintroduced into the pipe 10 using a sample pump 30. Further, the micro fluid injector comprises a carrier gas inlet 23 to which a source of a carrier gas 40, followed by a pressure regulator 41 is coupled. A sample outlet 24 of the micro fluid injector is connected to an inlet 51 of a miniaturized vaporizing unit 50.

The micro fluid injector further comprises a sample storage section 25 and an injector valve body 26 which can be switched from a first position wherein the substance is flowing from the inlet 21 via the storage section 25 to the outlet 22 to a second position wherein the sample stored in the sample storage section 25 is provided to the sample outlet 24 by directing carrier gas from the carrier gas inlet 23 through the sample storage section and pushing a predetermined amount of the sample stored in the sample storage section 25 to the sample outlet 24.

Said predetermined amount is provided to the miniaturized vaporizing unit 50 which comprises a heated surface transferring heat to the liquid substance and thus vaporizing the liquid substance. The such vaporized substance is directed via an outlet 52 of the miniaturized vaporizing unit to an inlet 61 of a gas injector 60. The gas injector 60 is designed in a similar way as the micro fluid injector 20, having a carrier gas inlet 63, a waste outlet 62 and a sample outlet 64 and a sample storage section 65. The carrier gas inlet 63 is coupled to the source of the carrier gas 40 via a pressure regulator 42, a particle filter 43 and an optional precolumn 44.

The gas injector 60 extracts a predetermined amount from the flow of the vaporized substance and provides this predetermined amount via the sample outlet 64 to a separation column 70 wherein this amount of the substance is separated into a plurality of fractions each fraction comprising molecules of a specific molecular weight or of specific molecular weight range.

The fractions are provided to a miniaturized thermal conductivity sensor 80 and the thermal conductivity sensor 80 detects the time at which a fraction passes thus allowing to calculate a time interval between the switching of the injector to provide the sample to the separation column and the time at which a certain fraction passes the sensor. From this time interval a molecular weight (range) can be calculated associated to the fraction passing the sensor by comparing the time interval to a table associated to the properties of the separation column 70. Calculation is done in a central processing unit 90. The analyzed substance is directed to a carrier out 81 and the results are provided to a personal computer 91 for displaying or storing it.

Figure 1A:
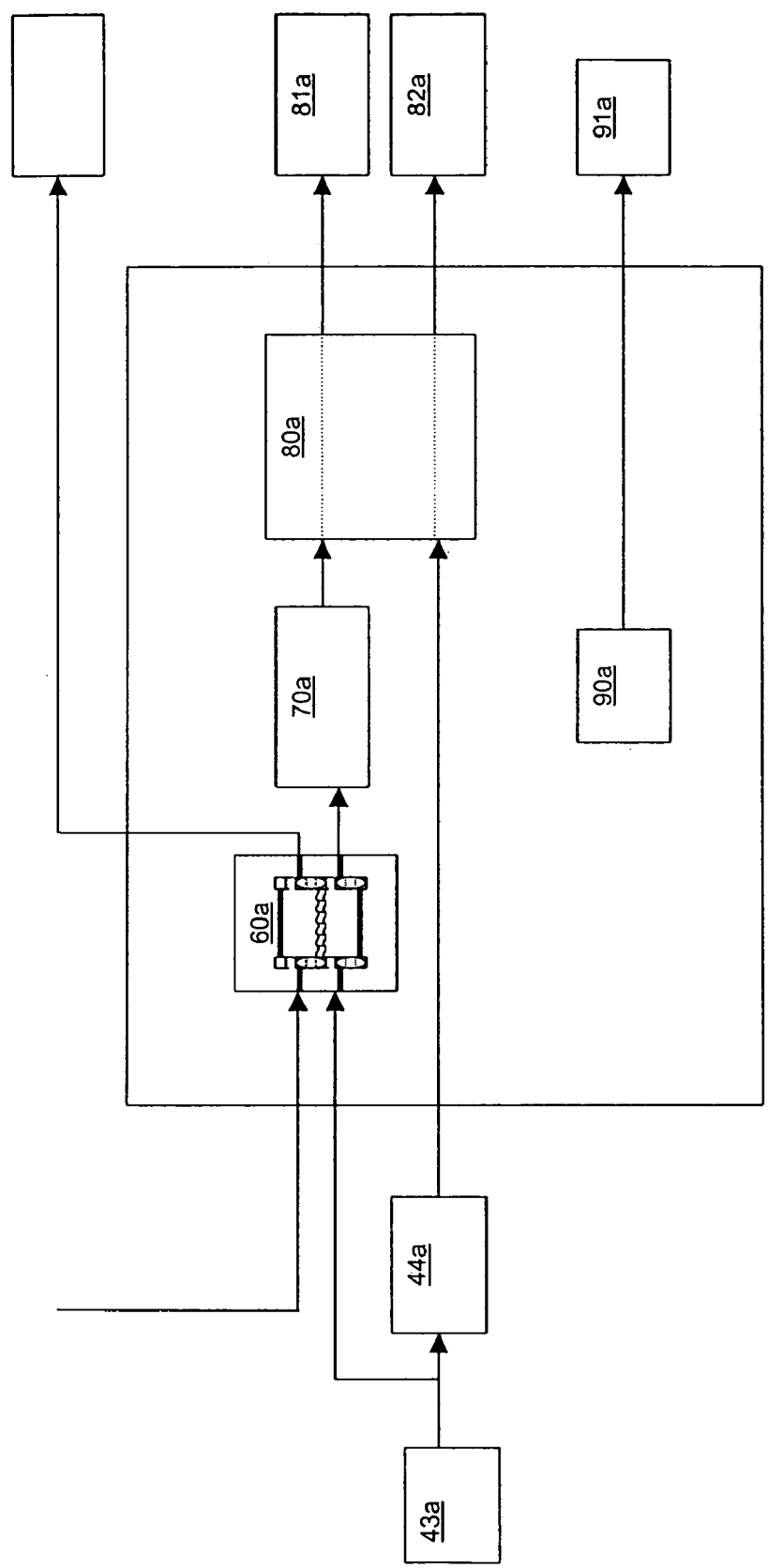

FIG. 1a shows a detailed view of the lower right part of the embodiment shown in FIG. 1 in a first variant. As can be seen from FIG. 1a, the carrier gas is distributed behind the particle filter 43a and a first portion is directed to a pre-column 44a which serves to affect a parallel heating of the carrier gas as in the separation column 70a. Another portion of the carrier gas is directed to the gas injector 60a. The sample exiting gas injector 60a is guided via the separation column 70a to the thermal conductivity sensor 80a. In a parallel line the carrier gas exiting the pre-column 44a is directed to the thermal conductivity sensor 80a. Within the thermal conductivity sensor 80a, a first pair of measurement filaments is arranged with a second pair of reference filaments in a wheat stone bridge. The filaments are coupled in the wheat stone bridge in such a way that temperature variations are compensated in that the carrier gas exiting the per-column 44a are directed to the reference filaments whereas the sample gas exiting the separation column 70a are directed to the measurement filaments.

Hereafter, the sample gas is directed to the carrier out 81a whereas the carrier gas exiting the thermal conductivity sensor 80a from the reference filaments is directed to an additional carrier gas exit 82a.

As described beforehand, a central processing unit 90a and a personal computer 91a is provided.

Figure 1B:
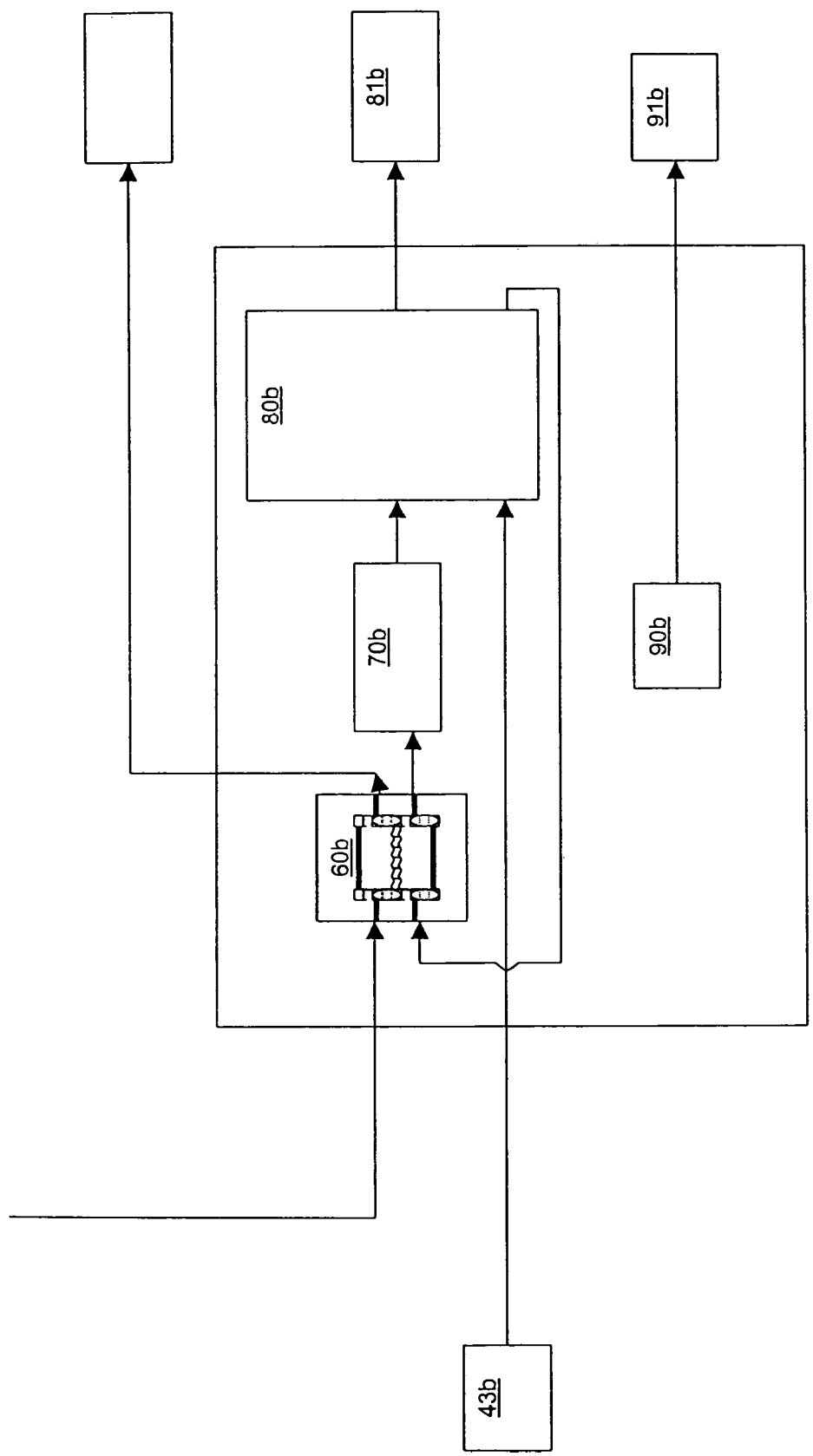

FIG. 1b shows an alternative embodiment to FIG. 1a which may replace the arrangement shown in the lower right of FIG. 1. As shown in FIG. 1b a pre-column is not present but the carrier gas is directed from the particle filter 43b directly to the reference filaments of the thermal conductivity sensor 80b. After exiting the thermal conductivity sensor 80b, the carrier gas is directed to the carrier gas inlet of the injector 60b and used to force the sample to the separation column 70b to the thermal conductivity sensor 80b. The sample exits the thermal conductivity sensor 80b to the carrier out 81b.

As described before, a central processing unit 90b coupled to a personal computer 91b is provided.

FIG. 2 shows an improved arrangement and method for analysing liquid substances. Method steps and components associated to such steps which are corresponding to those methods and components described in FIG. 1 are provided with reference signs increased by 100 to those of FIG. 1. As can be seen, a fluid sample 110 is provided to a micro fluid injector 120, from which predetermined amount is extracted from the continuous flow of the substance and this predetermined amount is provided to a miniaturized vaporizing unit 150.

From this miniaturized vaporizing unit 150 the vaporized substance is provided to a gas injector 160, extracting a predetermined amount from this gaseous flow and providing the predetermined amount to a separation column 170. The separation column 170 separated the sample into a plurality of fractions which fractions are analyzed in a thermal conductivity sensor 180.

The embodiment shown in FIG. 2 differs from that of FIG. 1 in that from the exit of the thermal conductivity sensor 180 the fractions are not directed to a sample outlet, i.e. a waste outlet, but instead are directed to a four port valve 260. The four port valve comprises an inlet 261 and an outlet 262 which are coupled to each other in a first position of the four port valve thus directing the fractions introduced into the inlet 261 to a waste exit. Further, a carrier gas inlet 223 is provided which is coupled to a sample outlet 224 in the first position of the four port valve.

The four port valve 260 can be switched to a second position wherein the sample inlet 261 is coupled to the sample outlet 264 thus directing a specific fraction or a specific plurality of fractions to the sample outlet. This specific fraction/these specific fractions is/are selected to be analyzed further. After the fractions have been directed to the sample outlet and have left the four port valve 260, the four port valve is switched back to the first position so that the carrier gas further pushes the fractions to a separation column 270.

The separation column 270 is designed to separate the fractions further and thus is specifically adapted to the molecular weight range of these fractions.

The such separated fractions, now being separated into a plurality of sub-fractions are provided to a thermal conductivity sensor 280 and thus the time difference between the arrival of each sub-fraction in the thermal conductivity sensor 280 and the time the four port valve was switched to the second position can be determined and from this time interval the molecular weight of the respective sub-fraction can be determined by comparing the time interval to pre-stored time intervals in a table corresponding to the properties of the separation column 270, as described beforehand.

Hereafter, the sample may be directed to a waste outlet thus finishing the analysis or a further four port valve 360 may be added to again extract one or more of the sub-fractions and direct these sub-fractions to a further separation column to provide additional analysis. It is to be understood that the such disclosed arrangement can be designed in a cascaded manner comprising a plurality of supplemental analyzing units each comprising a four port valve, a separation column and a thermal conductivity sensor.

FIG. 3 shows a third embodiment adapted to sequentially analyze a gaseous sample in a two-stage serial process.

The gaseous sample 410 is provided via a pressure regulator 411 to a gas injector 420.

The gas injector 420 receives carrier gas from a source of a carrier gas 440 via a particle filter 443 and a pressure regulator 442. The gas injector 420 extracts a pre-determined amount of the sample and provides said amount to a separation column 470 separating the sample amount into a plurality of fractions. The passing of these fractions is analyzed in a thermal conductivity sensor 480 thus allowing to calculate a time interval between the switching of the gas injector 420 and the passing of a specific fraction. From this time interval a molecular weight or molecular weight range of the specific fraction can be calculated as described beforehand.

A 2/2-way valve 560 is coupled to the thermal conductivity sensor 480 receiving the sample fractions. The 2/2-way valve 560 is switched in such a way to direct selected fractions to a waste exit 562 which fractions shall not be analyzed further. Selected other fractions are directed to a sample outlet 564 coupled to a second separation column 570 which is a packed column. The fraction or fractions directed to the second separation column are investigated further by separating them into a plurality of sub-fractions in the packed column and detecting the time order of these sub-fractions in a thermal conductivity sensor 580.

To drive the sub-fractions through the second separation column 570 the 2/2-way valve 560 is receiving filtered carrier gas from the carrier gas source 440 via the particular filter 443 and an additional pressure regulator 444.

A central processing unit 490 is provided to control switching of the injector 420, the 2/2-way valve 560 and to calculate the time intervals from the sensor signals of the thermal conductivity sensor 480 and 580. The values calculated by the central processing unit 490 are provided to a personal computer 491 for storing and displaying them to a user of the device.

FIG. 4 shows an exemplary arrangement of the components used for the analyzing process according to the invention and included in an analyzing module according to the invention. As can be seen from FIG. 4, an injector adapted to inject liquid or gaseous substances 420 is provided adjacent to a vaporizing unit or separation column 650. A gas injector 760 is arranged close to the vaporizing unit or separation column 650. Finally, a further separation column 770 is arranged adjacent to this gas injector.

A first thermal conductivity sensor 680 is provided associated to the vaporizing unit or separation column 650 and which is in use for analyzing fractions separated by the separation column 550. A second thermal conductivity sensor 780 is provided associated to the separation column 770 for analyzing the fractions or sub-fractions separated by the separation column 770.

FIG. 5 schematically depicts the principal of the serial analysis according to the invention. A first separation column 1070 separates a sample into a number of fractions 1011-1014.

Fractions 1012-1014 are sufficiently separated in the first separation column, e.g. by separating $C_3H_8$, $C_4H_{10}$ (propane, butane) and hydrocarbons of higher grade from each other. Fraction 1011 still contains a mixture of different substances and is provided to a second separation column 1170.

This second separation column 1170 is a packed column adapted to specifically separate within the molecular weight range of these substances. The second separation column 1170 separates fraction 1011 further in sub-fractions 1111-1114.

Sub-fractions 1112-1114 are sufficiently separated in the second separation column, e.g. by separating $CH_4$, $CO_2$, $C_2H_6$. Sub fraction 1111 still comprises a mixture of different substances which are not sufficiently separated and is provided to a third packed separation column 1270 which further separates these substances into sub-sub-fractions 1211-1215. These sub-sub-fractions, e.g. $N_2$, $O_2$, $CO$, $H_2$ are the final result of the analysis and thus detailed information about substances of high molecular weight down to substances of very low molecular weights of the molecules contained in the substance provided to the separation column 1070 initially are provided to the user.

The invention claimed is:

1. A miniaturized gas chromatography module, comprising:
    a gas injector unit having a gas injector sample inlet and outlet, the gas injector sample inlet being connectable with a source of a substance to be analysed,
    a separation column having a separation column inlet and outlet, the separation column inlet being in fluid communication with the gas injector sample outlet,
    a thermal conductivity sensor having a sensor inlet and outlet, the sensor inlet being in fluid communication with the separation column outlet, characterized by
    a pre-stage injector having a pre-stage injector sample inlet and outlet, the pre-stage injector sample inlet being connectable with the source of the substance to be analysed,
    a pre-stage module having a module inlet and outlet, the module inlet being in fluid communication with the pre-stage injector sample outlet and the module outlet being in fluid communication with the gas injector inlet,
    wherein the pre-stage module is adapted to transfer heat to a substance flowing from the module inlet to the module outlet;
    and wherein the pre-stage injector is adapted to provide a predetermined amount of a liquid substance to the pre-stage module and the pre-stage module is adapted to vaporize said amount of the liquid substance and provide the vaporized substance to the gas injector.

2. The module according to claim 1, wherein the gas injector is a four port valve having a first valve inlet in fluid communication with the outlet of the pre-stage separation column, a second valve inlet in fluid communication with a source of a carrier gas, a first valve outlet in fluid communication with the separation column inlet, a second valve outlet in fluid communication with a waste exit and a valve body coupling in a first position the first valve inlet to the second valve outlet and in a second position the first valve inlet to the second valve outlet.

3. The module according to claim 1, further comprising at least one supplemental analysing unit, the analysing unit comprising:
    a supplemental valve unit having a supplemental valve inlet and outlet, a supplemental separation column having a supplemental column inlet and outlet, the supplemental column inlet being in fluid communication with the supplemental valve outlet, a supplemental thermal conductivity sensor having a supplemental sensor inlet and outlet, the supplemental sensor inlet being in fluid communication with the supplemental column outlet.

4. The module according to claim 3, further comprising a plurality of supplemental analysing units wherein the plurality of units are connected in series to each other by providing a fluid communication between the supplemental sensor outlet of a preceding, supplemental analysing unit to the supplemental valve inlet of a following supplemental analyzing unit.

5. The module according to claim 1, further comprising:
a distribution valve unit, said valve unit having a distribution valve inlet and a plurality of distribution valve outlets and
a plurality of parallel supplemental analysing units, each analysing unit comprising:
a supplemental separation column having a supplemental column inlet and outlet, the supplemental column inlet being in fluid communication with an outlet of the distribution supplemental valve,
a supplemental thermal conductivity sensor having a supplemental sensor inlet and outlet, the supplemental sensor inlet being in fluid communication with the supplemental column outlet,
a control device adapted to receive a signal from the pre-stage thermal conductivity sensor and to switch the distribution valve between a plurality of positions to sequentially provide a selected fraction of the gas to each distribution valve outlet.

6. The module according to claim 5, wherein at least one of the supplemental thermal conductivity sensors of the parallel supplemental analysing units is followed by at least one supplemental analysing unit coupled in series to each other by providing a fluid communication between the supplemental sensor outlet of a preceding, supplemental analysing unit to the supplemental valve inlet of a following supplemental analysing unit.

7. The module according to claim 1, wherein the pre-stage injector further comprises:
a pre-stage injector carrier gas inlet connectable to a source of a carrier gas,
a pre-stage injector waste outlet connectable to a waste exit or connectable to the source of the substance to be analysed,
wherein the inlets and outlets are provided in an injector housing, the housing further comprising
a moveable injector body which can be moved from a first injector body position wherein the substance to be analysed is flowing from the pre-stage injector sample inlet through a sample storage section to the pre-stage waste outlet and a second injector body position wherein the carrier gas is flowing from the pre-stage injector carrier gas inlet through the sample storage section to the pre-stage injector sample outlet thus providing a predetermined amount of the substance to be analysed to the pre-stage injector sample outlet.

8. The module according to claim 1, wherein the gas injector further comprises:
a gas injector carrier gas inlet connectable to a source of a carrier gas,
a gas injector waste outlet connectable to a waste exit or connectable to the source of the substance to be analysed,
wherein the inlets and outlets of the gas injector are provided in an injector housing, the housing further comprising
a moveable injector body which can be moved from a first injector body position wherein the substance to be analysed is flowing from the gas injector sample inlet through a sample storage section to the gas waste outlet and a second injector body position wherein the carrier gas is flowing from the gas injector carrier gas inlet through the sample storage section to the gas injector sample outlet thus providing a predetermined amount of the substance to be analysed to the gas injector sample outlet.

9. A method of analysing a substance, comprising the steps of:
providing a flow of the substance to a gas injector sample inlet of a gas injector unit,
extracting a predetermined amount from the flow of the substance by the gas injector unit and providing said amount from a gas injector sample outlet to a separation column inlet of a separation column,
separating said amount into a plurality of fractions of the substance by the separation column and providing said fractions to a sensor inlet of a thermal conductivity sensor,
determining the time intervals between the time at which the extracted amount of the substance was provided from the gas injector to the separation column and the time at which each fraction passes the thermal conductivity sensor, and
comparing the time intervals with pre-known time intervals stored in a list associated with pre-known substances and thus identifying the substance contained in each fraction,
characterized in that before providing the substance to the gas injector unit the following steps are conducted
providing a continuous flow of the substance to a pre-stage injector inlet of a pre-stage injector,
extracting a predetermined amount from the continuous flow by the pre-stage injector and providing said amount to a module inlet of a pre-stage module,
transferring heat from a surface of the pre-stage module to said amount of said substance, and
providing said amount of said substance from an outlet of said pre-stage module to said gas injector inlet
and wherein the substance provided to the pre-stage injector is a liquid substance, said amount of said liquid substance is vaporized in said pre-stage module and the vaporized liquid is provided to the gas injector.

10. The method according to claim 9, wherein at least one selected fraction, but not all fractions, are further analysed in at least one supplemental analysing unit by:
providing all fractions from the outlet of the thermal conductivity sensor to an inlet of a supplemental valve unit,
extracting said selected fraction(s) by said supplemental valve unit and providing said selected fraction(s) to a supplemental separation column,
separating said fractions(s) into a plurality of sub-fractions of the substance by the supplemental separation column and providing said sub- fractions to a sensor inlet of a supplemental thermal conductivity sensor,
determining the time intervals between the time at which said selected fraction(s) of the substance was/were provided to the supplemental separation column and the time at which each sub-fraction passes the supplemental thermal conductivity sensor, and comparing the time intervals with pre-known time intervals stored in a list associated with pre-known substances and thus identifying the substance contained in each sub-fraction.

11. The method according to claim 10, wherein said fractions are analysed in a plurality of supplemental analysing units connected in series to each other by providing a fluid communication between the supplemental sensor outlet of a preceding, supplemental analysing unit to the supplemental valve inlet of a following supplemental analysing unit.

12. A miniaturized gas chromatography module, comprising:
a gas injector unit having a gas injector sample inlet and outlet, the gas injector sample inlet being connectable with a source of a substance to be analysed,
a separation column having a separation column inlet and outlet, the separation column inlet being in fluid communication with the gas injector sample outlet, and
a thermal conductivity sensor having a sensor inlet and outlet, the sensor inlet being in fluid communication with the separation column outlet, characterized by
a pre-stage injector having a pre-stage injector sample inlet and outlet, the pre-stage injector sample inlet being connectable with the source of the substance to be analysed, and
a pre-stage module having a module inlet and outlet, the module inlet being in fluid communication with the pre-stage injector sample outlet and the module outlet being in fluid communication with the gas injector inlet,
wherein the pre-stage module is adapted to transfer heat to a substance flowing from the module inlet to the module outlet;
and wherein the pre-stage injector is adapted to provide a predetermined amount of a gaseous substance to the pre-stage module, wherein the pre-stage module is a pre-stage separation column adapted to separate the flow of gas into a plurality of fractions and to sequentially provide said fractions to said gas injector.

13. The module according to claim 12, wherein the gas injector is a four port valve having a first valve inlet in fluid communication with the outlet of the pre-stage separation column, a second valve inlet in fluid communication with a source of a carrier gas, a first valve outlet in fluid communication with the separation column inlet, a second valve outlet in fluid communication with a waste exit and a valve body coupling in a first position the first valve inlet to the second valve outlet and in a second position the first valve inlet to the second valve outlet.

14. The module according to claim 12, further comprising a pre-stage thermal conductivity sensor coupled between the pre-stage separation column outlet and the first valve inlet to analyze fractions of the substance as provided by the pre-stage separation column, a control device adapted to receive a signal from the pre-stage thermal conductivity sensor and to switch the four port valve between the first and second position to provide a selected fraction of the gas to the separation column inlet.

15. The module according to claim 12, further comprising at least one supplemental analysing unit, the analysing unit comprising:
a supplemental valve unit having a supplemental valve inlet and outlet,
a supplemental separation column having a supplemental column inlet and outlet, the supplemental column inlet being in fluid communication with the supplemental valve outlet, and a supplemental thermal conductivity sensor having a supplemental sensor inlet and outlet, the supplemental sensor inlet being in fluid communication with the supplemental column outlet.

16. The module according to claim 12, further comprising a plurality of supplemental analysing units wherein the plurality of units are connected in series to each other by providing a fluid communication between the supplemental sensor outlet of a preceding, supplemental analysing unit to the supplemental valve inlet of a following supplemental analysing unit.

17. The module according to claim 12, further comprising:
a distribution valve unit, said valve unit having a distribution valve inlet and a plurality of distribution valve outlets and
a plurality of parallel supplemental analysing units, each analysing unit comprising:
a supplemental separation column having a supplemental column inlet and outlet, the supplemental column inlet being in fluid communication with an outlet of the distribution supplemental valve,
a supplemental thermal conductivity sensor having a supplemental sensor inlet and outlet, the supplemental sensor inlet being in fluid communication with the supplemental column outlet, and a control device adapted to receive a signal from the pre-stage thermal conductivity sensor and to switch the distribution valve between a plurality of positions to sequentially provide a selected fraction of the gas to each distribution valve outlet.

18. The module according to claim 12, wherein at least one of the supplemental thermal conductivity sensors of the parallel supplemental analysing units is followed by at least one supplemental analysing unit coupled in series to each other by providing a fluid communication between the supplemental sensor outlet of a preceding, supplemental analysing unit to the supplemental valve inlet of a following supplemental analysing unit.

19. The module according to claim 12, wherein the pre-stage injector further comprises:
a pre-stage injector carrier gas inlet connectable to a source of a carrier gas, and
a pre-stage injector waste outlet connectable to a waste exit or connectable to the source of the substance to be analysed,
wherein the inlets and outlets are provided in an injector housing, the housing further comprising
a moveable injector body which can be moved from a first injector body position wherein the substance to be analysed is flowing from the pre-stage injector sample inlet through a sample storage section to the pre-stage waste outlet and a second injector body position wherein the carrier gas is flowing from the pre-stage injector carrier gas inlet through the sample storage section to the pre-stage injector sample outlet thus providing a predetermined amount of the substance to be analysed to the pre-stage injector sample outlet.

20. The module according to claim 12, wherein the gas injector further comprises:
a gas injector carrier gas inlet connectable to a source of a carrier gas, and
a gas injector waste outlet connectable to a waste exit or connectable to the source of the substance to be analysed,
wherein the inlets and outlets of the gas injector are provided in an injector housing, the housing further comprising
a moveable injector body which can be moved from a first injector body position wherein the substance to be analysed is flowing from the gas injector sample inlet through a sample storage section to the gas waste outlet and a second injector body position wherein the carrier gas is flowing from the gas injector carrier gas inlet through the sample storage section to the gas injector sample outlet thus providing a predetermined amount of the substance to be analysed to the gas injector sample outlet.

21. A method of analysing a substance, comprising the steps of:
providing a flow of the substance to a gas injector sample inlet of a gas injector unit,
extracting a predetermined amount from the flow of the substance by the gas injector unit and providing said amount from a gas injector sample outlet to a separation column inlet of a separation column,
separating said amount into a plurality of fractions of the substance by the separation column and providing said fractions to a sensor inlet of a thermal conductivity sensor,
determining the time intervals between the time at which the extracted amount of the substance was provided from the gas injector to the separation column and the time at which each fraction passes the thermal conductivity sensor, and
comparing the time intervals with pre-known time intervals stored in a list associated with pre-known substances and thus identifying the substance contained in each fraction,
characterized in that before providing the substance to the gas injector unit the following steps are conducted:
providing a continuous flow of the substance to a pre-stage injector inlet of a pre-stage injector,
extracting a predetermined amount from the continuous flow by the pre-stage injector and providing said amount to a module inlet of a pre-stage module,
transferring heat from a surface of the pre-stage module to said amount of said substance, and
providing said amount of said substance from an outlet of said pre-stage module to said gas injector inlet;
and wherein said substance provided to said pre-stage injector is gaseous, wherein said amount of said gaseous substance is separated into a plurality of fractions in said pre-stage Module being a pre-stage separation column, said fractions are sequentially provided to a pre-stage thermal conductivity sensor to analyse fractions of the substance as provided by the pre-stage separation column, said fractions are provided from the pre-stage thermal conductivity sensor to the gas injector and at least one selected fraction, but not all fractions, are provided to the separation column inlet, wherein a control device receives a signal from the pre-stage thermal conductivity sensor and switches the gas injector to provide said selected fractions of the gas to the separation column inlet.

22. The method according to claim 21, wherein at least one selected fraction, but not all fractions, are further analysed in at least one supplemental analysing unit by:
providing all fractions from the outlet of the thermal conductivity sensor to an inlet of a supplemental valve unit,
extracting said selected fraction(s) by said supplemental valve unit and providing said selected fraction(s) to a supplemental separation column,
separating said fractions(s) into a plurality of sub-fractions of the substance by the supplemental separation column and providing said sub- fractions to a sensor inlet of a supplemental thermal conductivity sensor,
determining the time intervals between the time at which said selected fraction(s) of the substance was/were provided to the supplemental separation column and the time at which each sub-fraction passes the supplemental thermal conductivity sensor, and
comparing the time intervals with pre-known time intervals stored in a list associated with pre-known substances and thus identifying the substance contained in each sub-fraction.

23. The method according to claim 22, wherein said fractions are analysed in a plurality of supplemental analysing units connected in series to each other by providing a fluid communication between the supplemental sensor outlet of a preceding, supplemental analysing unit to the supplemental valve inlet of a following supplemental analysing unit.

* * * * *